United States Patent
Siewerdsen et al.

(10) Patent No.: US 11,478,214 B2
(45) Date of Patent: Oct. 25, 2022

(54) GEOMETRIC CALIBRATION FOR CONE BEAM CT USING LINE FIDUCIALS

(71) Applicant: THE JOHNS HOPKINS UNIVERSITY, Baltimore, MD (US)

(72) Inventors: Jeffrey H. Siewerdsen, Baltimore, MD (US); Matthew W. Jacobson, Baltimore, MD (US); Michael Ketcha, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/494,439

(22) PCT Filed: Mar. 16, 2018

(86) PCT No.: PCT/US2018/022809
§ 371 (c)(1),
(2) Date: Sep. 16, 2019

(87) PCT Pub. No.: WO2018/170366
PCT Pub. Date: Sep. 20, 2018

(65) Prior Publication Data
US 2020/0085404 A1   Mar. 19, 2020

Related U.S. Application Data

(60) Provisional application No. 62/472,178, filed on Mar. 16, 2017.

(51) Int. Cl.
*A61B 6/03* (2006.01)
*A61B 6/00* (2006.01)
(Continued)

(52) U.S. Cl.
CPC .............. *A61B 6/584* (2013.01); *A61B 6/025* (2013.01); *A61B 6/032* (2013.01); *A61B 6/4085* (2013.01);
(Continued)

(58) Field of Classification Search
None
See application file for complete search history.

(56) References Cited

U.S. PATENT DOCUMENTS

| | | |
|---|---|---|
| 6,049,582 A | 4/2000 | Navab |
| 2001/0053204 A1 | 12/2001 | Navab et al. |
| 2003/0007601 A1 | 1/2003 | Jaffray et al. |

(Continued)

OTHER PUBLICATIONS

Cho et al., "Accurate technique for complete geometric calibration of cone-beam computed tomography systems." Medical physics 32 (4) 968-83 (2005).
Daly et al., "Geometric calibration of a mobile C-arm for intraoperative conebeam CT" Medical Physics 35 (5) 2124 (2008).
(Continued)

*Primary Examiner* — Hoon K Song
(74) *Attorney, Agent, or Firm* — Johns Hopkins Technology Ventures

(57) ABSTRACT

The present invention is directed to an alternative geometric calibration method based on a calibration phantom with multiple line-shaped markers. The markers can in some embodiments take the form of radio-opaque wires. Line fiducials overcome the occlusion hazards of spherical fiducials, because their projections overlap very mildly as long as the wires are mutually non-coplanar in 3D. This makes the phantom amenable to a wider range of orbits and less sensitive to phantom positioning. Equations relating the pose of 3D line-shaped objects to their 2D radiographic projections are then used as the basis for view-by-view geometry estimation. The technique can flexibly accommo- (Continued)

date a wide range of different CT scan trajectories, including strongly noncircular trajectories known to provide better image quality than standard circular scans.

20 Claims, 11 Drawing Sheets

(51) Int. Cl.
- G06T 7/80 (2017.01)
- G06T 7/73 (2017.01)
- A61B 6/02 (2006.01)
- G06T 7/60 (2017.01)

(52) U.S. Cl.
CPC .............. *G06T 7/60* (2013.01); *G06T 7/73* (2017.01); *G06T 7/80* (2017.01); *G06T 2207/10081* (2013.01); *G06T 2207/30204* (2013.01)

(56) References Cited

U.S. PATENT DOCUMENTS

| | | | |
|---|---|---|---|
| 2005/0008126 A1* | 1/2005 | Juh | A61B 6/583 378/207 |
| 2005/0117708 A1 | 6/2005 | Cho et al. | |
| 2017/0020481 A1* | 1/2017 | Hawker | A61B 6/584 |

OTHER PUBLICATIONS

He et al., (2008). Camera calibration from vanishing points in a vision system. Optics and Laser Technology, 40(3), 555-561.
Caprile et al., (1990). Using vanishing points for camera calibration. International Journal of Computer Vision, 4(2), 127-139.
Cipolla et al., (1999). Camera calibration from vanishing points in images of architectural scenes. Review Literature and Arts of The Americas, 2, 382-391.
Bernhard, E., "Geometry Calibration Phantom Design for 3D Imaging" Medical Imaging 2006: Physics of Medical Imaging, Proceedings of SPIE vol. 6142, 61422E, (2006).

* cited by examiner

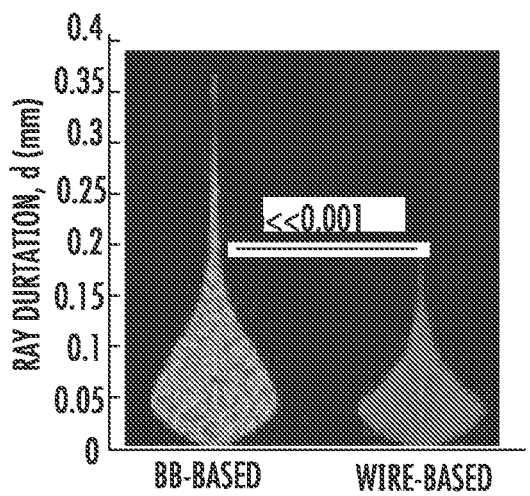
FIG. 9A
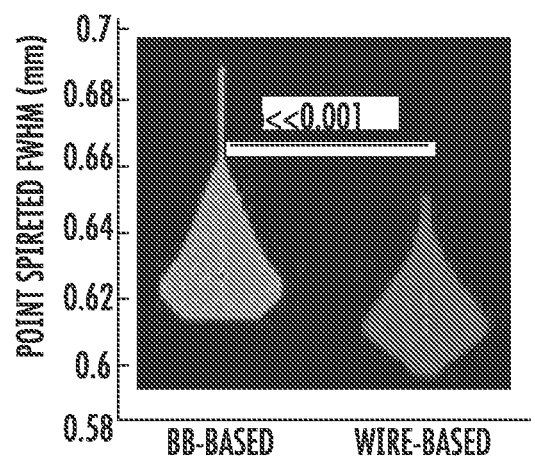
FIG. 9B
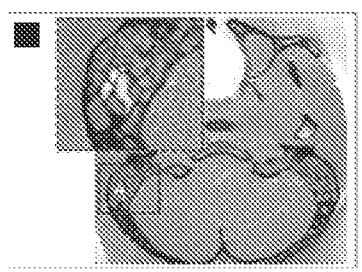 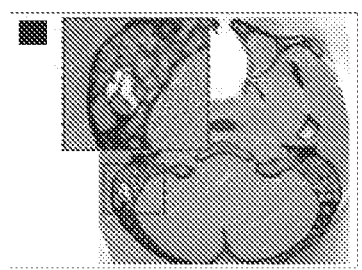
FIG. 9C   FIG. 9D

GEOMETRIC CALIBRATION FOR CONE BEAM CT USING LINE FIDUCIALS

CROSS-REFERENCE TO RELATED APPLICATIONS

This application is a 35 U.S.C. § 371 U.S. national entry of International Application PCT/US2018/022809, having an international filing date of Mar. 16, 2018, which claims the benefit of U.S. Provisional Application No. 62/472,178, filed Mar. 16, 2017, the content of each of the aforementioned applications is herein incorporated by reference in their entirety.

GOVERNMENT SUPPORT

This invention was made with Government support under grant number EB017226 awarded by the National Institutes of Health. The Government has certain rights in the invention.

FIELD OF THE INVENTION

The present invention relates generally to medical imaging. More particularly, the present invention relates to a method for geometric calibration for cone beam CT using line fiducials.

BACKGROUND OF THE INVENTION

Geometric calibration is the process of identifying a cone-beam CT (CBCT) system projection geometry, i.e., the relationship between 3D points and their projected locations at various gantry positions. The relationship depends on system geometric parameters such as the Source-Detector Distance (SDD) and the orientation of the detector panel in each projection view. Most commonly, geometric calibration is performed by scanning a known 3D configuration of radio-opaque spherical fiducials, such as the phantom in FIG. 1A. By observing the projected locations of the fiducials, the system geometry may be deduced in various ways. In recent years, alternative "online" calibration methods have been proposed that can deduce geometry directly from a patient scan. However, these methods tend to be demanding computationally or to rely on specific assumptions about the orbit shape. Offline phantom-based calibration methods are still preferred, due to their relatively simple computational and hardware requirements.

A problem with spherical marker phantoms, however, is that they are often customized to relatively restricted orbit shapes and ranges of gantry motion. Phantom and software customization is needed either to avoid or to contend with marker projection overlap, of the kind marked by an arrow in FIG. 1A. When overlap occurs, accurate determination of shadow locations is compromised, potentially degrading calibration accuracy. Moreover, overlap makes it difficult to perform 3D-2D marker matching steps typically required by calibration algorithms.

Accordingly, there is a need in the art for geometric calibration for cone beam CT using line fiducials. Line fiducials are resilient to problems.

SUMMARY OF THE INVENTION

The foregoing needs are met, to a great extent, by the present invention which provides a method of calibration for a computed tomography scanner including providing line shaped markers for the computed tomography scanner. The computed tomography scanner to be calibrated can include a circular orbit or a non-circular orbit. The method also includes programming a non-transitory computer readable medium to execute steps including describing a 3D pose of the line shaped marker, extracting sample points along a 2D shadow of each of the line shaped markers to map the 3D line to a 2D line, and estimating geometric parameters for the tomography scanner from this data.

In accordance with an aspect of the present invention, the computed tomography scanner has a sinusoidal orbit. The geometric parameters are estimated by minimizing a least squares cost function. Additionally, the line shaped markers take the form of radiopaque wires.

In accordance with another aspect of the present invention, a system for calibration for a computed tomography scanner includes line shaped markers for the computed tomography scanner. The computed tomography scanner to be calibrated can have a circular orbit or a non-circular orbit. The system also includes a non-transitory computer readable medium programmed to execute steps including describing a 3D pose of the line shaped marker, extracting sample points along a 2D shadow of each of the line shaped markers to map the 3D line to a 2D line, and estimating geometric parameters for the tomography scanner from this data.

In accordance with still another aspect of the present invention the tomography scanner can have a sinusoidal orbit. The non-transitory computer readable medium is programmed for estimating the geometric parameters by minimizing a least squares cost function. The line shaped markers take the form of radiopaque wires. The computed tomography scanner has a circular or non-circular orbit or is capable of multiple orbits of different shapes. The computed tomography scanner takes the form of one selected from a group consisting of a computed tomography scanner and a cone-beam computed tomography scanner. The non-transitory computer readable medium is programmed for executing pose determination. The system also includes executing pose determination from a limited orbit.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 1A illustrates a BB phantom with a pair of overlapping marker shadows marked by arrow. FIG. 1B illustrates a proposed wire fiducial phantom, according to an embodiment of the present invention.

FIG. 4A illustrates a graphical view of a maximum marker BPE per view for each calibration method. FIG. 4B illustrates an FDK head reconstruction based on BB phantom calibration. FIG. 4C illustrates an FDK head reconstruction based on multi-wire phantom calibration.

FIG. 5A illustrates a reconstructions of the head phantom in both a circular and sinusoidal orbit. FIG. 5B illustrates a graphical view of edge resolution at disk edges as a function of distance from the central axial plane for different orbits.

FIG. 6A illustrates a sampling of gantry poses in spherical coordinates used in calibration accuracy simulation tests. FIG. 6B illustrates a triangulation ray deviation metric.

FIG. 6C illustrates a digital head phantom with two stacks of high contrast disks. FIG. 6D illustrates a prototype mobile C-arm for cone beam CT based on the Cios Alpha. FIG. 6E illustrates a real head phantom with two stacks of polyethylene and Teflon® disks.

FIGS. 9A-9D illustrate image and graphical views of a comparison with BB-based calibration in a real circular scan orbit.

DETAILED DESCRIPTION

Figure 1A:
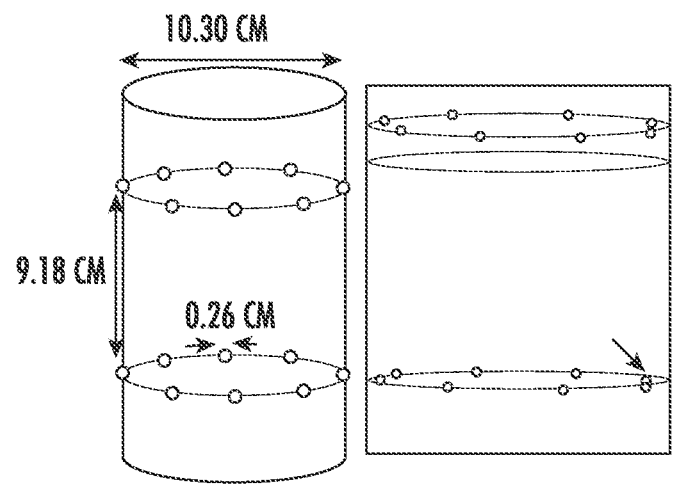
FIGS. 1A and 1B illustrate CBCT system geometry calibration phantoms, each with sample 2D projection views.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to an alternative geometric calibration method based on a calibration phantom containing multiple line-shaped markers. The line-shaped markers can in some embodiments take the form of radio-opaque wires. Line fiducials overcome the occlusion hazards of spherical fiducials, because their projections overlap very mildly as long as the wires are mutually non-coplanar in 3D. This makes the phantom amenable to a wider range of orbits and less sensitive to phantom positioning. Equations relating the pose of 3D line-shaped objects to their 2D radiographic projections are then used as the basis for view-by-view geometry estimation. The technique can flexibly accommodate a wide range of different CT scan trajectories, including strongly noncircular trajectories known to provide better image quality than standard circular scans.

Geometric calibration of cone-beam CT systems is traditionally accomplished by scanning a fixture of radio-opaque spherical markers (BBs), and deducing system geometry from the pattern of 2D projection shadows cast by the markers in the x-ray images. The novelty of the disclosed invention lies in the use of line-shaped markers as opposed to spheres or BBs. This overcomes several limitations of traditional calibration. The line-shaped markers or fiducials are used for geometric calibration and can be formed from segments of radio-opaque wire. Geometric parameter estimation is accomplished by relating the 3D line equations representing the wires to the 2D line equations of their projections. While line-shaped features have long been used for calibration of photographic cameras line fiducial methods have not been applied in CBCT calibration, to our knowledge.

The use of line fiducials is more generally adaptable to a diversity of non-circular orbits than traditional BB methods in at least 3 respects. First, 2D projections of 3D lines can intersect at no more than a single point, for any gantry pose, as long as the 3D lines are mutually non-coplanar. Since 2D line segment detection is not confounded by a single point of intersection, problems of fiducial overlap are avoided in a highly orbit-independent way. For technical reasons to be discussed below, the design of the present invention does include some coplanar wires, but by keeping these sufficiently spaced apart, the phantom is able to accommodate a significant range of circular and non-circular orbits. Second, because each wire projection is identified by two line segment endpoints, they lie far apart in a 4D feature space and can be robustly tracked from view-to-view for fiducial identification purposes. This is in contrast to BB projection tracking, which may be confounded if two BB projections overlap or lie in close proximity. When this occurs, the BBs may be misidentified in all subsequent views unless specific knowledge of the orbit geometry is used to resolve the ambiguity. Third, line-based calibration is less adversely affected if the phantom is not completely contained in the viewable region of the x-ray detector, a scenario that is likely to occur for at least some gantry positions in complicated orbit geometries. In such gantry positions, a BB near the edge of the phantom may be completely unviewable, and any information about the view geometry encoded in that particular BB is lost. Conversely, line fiducial phantoms can be designed so that all line markers extend deep into the center of the field of view, making them more robustly visible. Note that only a section of a line fiducial (not its whole length) need be visible for its 2D line equation to be determined and for constraining information on the projection geometry to be obtained.

The proposed invention is more flexible than traditional calibration methods in the range of CT scan geometries that can be handled by a given marker fixture. Such methods may be strictly tied to the assumption of a circular (or near-circular) orbit of the x-ray source and detector, making them poorly suited to more advanced cone beam CT systems that are not constrained to circular orbits. The method uses a line-to-line matching that is more robust against error in fiducial identification (cf., centroid estimation and single-point matching).

Another problem with traditional calibration based on BBs is that their x-ray projection shadows can strongly overlap, compromising calibration accuracy and 3D-2D marker labelling steps that calibration algorithms typically require. To deal with marker overlap scenarios, BB fixtures and calibration software must be tailored to a specific scan orbit shape. For example, the spacing and orientation of the BBs may be chosen to ensure that overlap will not occur for a particular orbit geometry under consideration. The use of line-objects, as disclosed here, overcomes these limitations. Line-shaped markers will always overlap very mildly, under any orbit geometry, provided that they have non-coplanar poses in the calibration fixture. This means that the same fixture and calibration software can be applied to a range of different orbits.

Compared to conventional BB fiducial markers, line markers are intrinsically richer fiducials and are more easily tracked from view to view, even in instances of missing line segment samples. Furthermore, the proposed phantom of the present invention is more flexible in its placement relative to principal axes (e.g., axis of rotation) of the CT system.

The proposed invention more naturally handles CT systems with restricted Field of View (FOV). CT systems with small area x-ray detectors will have a correspondingly small FOV. As a consequence, BB calibration fixtures must often be carefully centered in the FOV of these systems so that all markers are always visible to the CT camera during the calibration scan. In practice, this can lead to time-consuming manual effort and rescanning. Alternatively, some inventors have proposed calibration methods allowing the BB configuration to be partially viewable. This is done by ensuring that their projections form readable code words. However, these designs involve complicated configurations of markers that are expensive to fabricate. Conversely, line-shaped markers are always identifiable and can be tracked from one projection-view to the next as long as even a small segment of their x-ray shadows is visible in the x-ray projections.

In CBCT, the projection of a 3D coordinate to a 2D view coordinate is described by the equation x=PX. Here, X and x are 4×1 and 3×1 homogeneous coordinate vectors representing the 3D and 2D locations respectively. The parametric equation for a 3D line in homogeneous coordinates as L(t)=X+tD where X=[$X^T$, 1]$^T$ and D=[$D^T$, 1] are 4×1 homogeneous vectors representing, respectively, a point on the line and the line's direction. The 3×1 vectors X and D denote the same in inhomogeneous coordinates. The geometry of a flat panel detector cone-beam CT system in a particular gantry position can be specified by nine parameters. In the parametrization considered here, three of the nine parameters are the position coordinates of the x-ray source, expressed as the vector C=[$c_x$, $c_y$, $C_z$]$^T$. Three additional parameters are the Euler angles defining detector orientation expressed as the vector θ=[$θ_1$, $θ_2$, $θ_3$]$^T$. The final three are the so-called intrinsic parameters consisting of the source-detector distance (SDD) and the 2D piercing point coordinates ($u_0$, $v_0$) where C projects orthogonally to the detector. Let α=[SDD, $u_0$, $v_0$]$^T$ denote the vector of intrinsic parameters collectively.

The matrix P is a 3×4 projection matrix, for that particular projection view, with the following 9 degree of freedom decomposition, $$P = KR[1 \ -C], \quad (1)$$

$$K = \begin{bmatrix} SDD & 0 & u_0 \\ 0 & SDD & v_0 \\ 0 & 0 & 1 \end{bmatrix} \quad (2)$$

In these equations, SDD is the Source-Detector distance, ($u_0$, $v_0$) are 2D image coordinates where the focal spot projects orthogonally onto the detector (the so-called piercing point), R is a 3×3 orthogonal matrix whose rows are the detector axes, and C is a 3×1 vector representing the 3D location of the focal spot.

A 3D line can be parametrized by two points on the line, represented by 4×1 homogeneous vectors X=[$\tilde{X}^T$, 1]$^T$ and Y=[$\tilde{Y}^T$, 1]$^T$. Under cone-beam projection, the 3D line maps to a 2D line whose equation a u+b v+c=0 is compactly expressed as $l^T$x=0. Here l=[a, b, c]$^T$ and x=[u, v, 1]$^T$ are homogeneous vectors representing the 2D line itself and a point on the line, respectively. Since X and Y are points on the 3D line, they project to points satisfying the 2D line equation, leading to, $$l^T P[X,Y]=0 \quad (3)$$

Put another way, l is orthogonal to both PX and PY and is therefore given by their cross-product l=PX×PY. Incorporating (1) then leads to the following explicit form for l, $$l=K^{-T}R(C×(\tilde{X}-\tilde{Y})+(\tilde{X}×\tilde{Y})) \quad (4)$$

where irrelevant scale factors are ignored.

In a method of the proposed invention, scans of a multi-wire phantom are acquired and sample points along their 2D line shadows are extracted. Equation (4) is then used as a basis for estimating, for each acquired view, the geometric entities K, R, and C. It is assumed that the 3D phantom geometry is known.

For each fixed wire, i, a pair of 3D points $X_i$, $Y_i$ is needed to describe the wire's 3D pose. Obtaining these 3D point pairs is an offline step that uses a standard CBCT scan of the phantom on an already-calibrated system or another accurate 3D representation of the phantom. Samples of the i-th line shadow are extracted from the acquired views (see next) and a line fit is performed to obtain an equation vector, l. This is done in each projection view. Equation (3) then provides a set of linear equations in X and Y (two per view), which is solved algebraically to obtain $X_i$ and $Y_i$.

For each fixed wire, i, sample points $x_{ij}$ lying on the 2D line shadow $l_i$ are to be extracted. Any line segment detection method would serve this purpose. In one exemplary implementation, a binary map of the line shadows in each view is obtained by thresholding. Morphological operations are then applied to detect and remove intersection points of the line shadows from the binary map. Next, region growing is used to group high-attenuation pixels in the remaining sub-segments. Finally, a search is made to determine which sub-segments belong to the same wire. This is done by comparing the subs-segments pair-wise for proximity and collinearity.

The geometry parameters in each fixed projection view are estimated by minimizing the following least squares cost function, motivated by equation (4), $$f(\alpha, \theta, C) = \sum_{ij} \left\| x_{ij}^T K_\alpha^{-T} R_\theta (C×(\tilde{X}_i - \tilde{Y}_i) + (\tilde{X}_i × \tilde{Y}_i)) \right\|^2 \quad (5)$$

Here α=[SDD, $u_0$, $v_0$]$^T$ is a parametrization of K, and θ is a 3×1 vector of Euler angles parametrizing R. The cost function reaches a value of zero, due to (4), when the samples $x_{ij}$ lie on the line $l_i$ exactly.

Figure 1B:
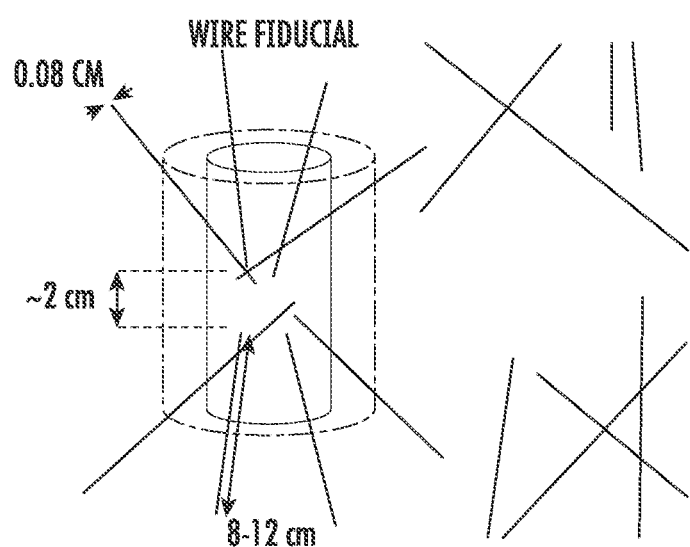
Figure 1C:
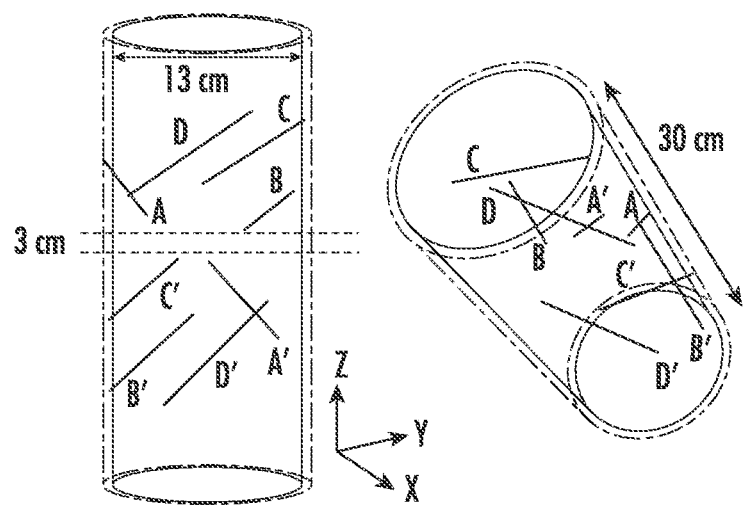
FIGS. 1C and 1D illustrate wire calibration phantoms, according to an embodiment of the present invention.
Figure 1D:
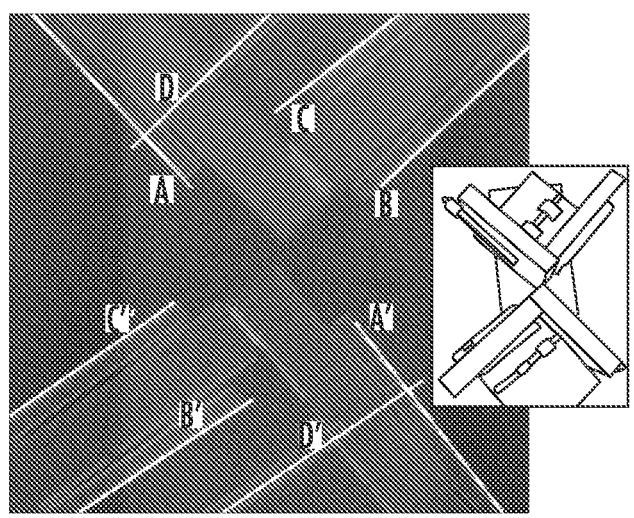

FIGS. 1C and 1D illustrate wire calibration phantoms, according to an embodiment of the present invention. FIG. 1C illustrates a CAD rendering of a nominal 8-wire phantom design, and FIG. 1D illustrates a photo and projection view of the 8-wire phantom experiment prototype.

Figure 2A:
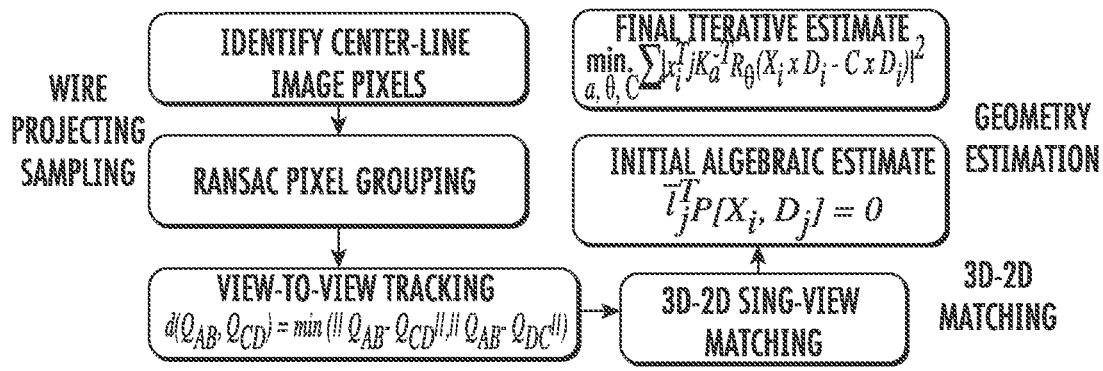
FIG. 2A illustrates a flowchart of a wire-based calibration method of the present invention.
Figure 2B:
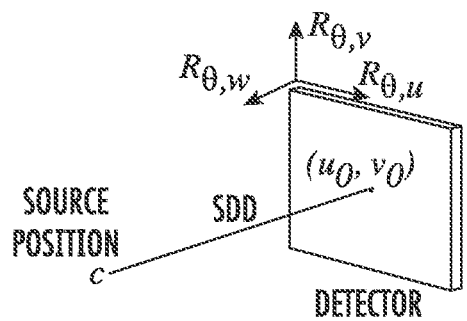
FIG. 2B illustrates a graphical view of parameterization of 9-DOF projection view geometry.
Figure 2C:
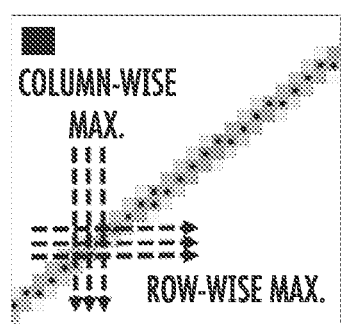
FIG. 2C illustrates a view of a sampling of wire segment projections.
Figure 2D:
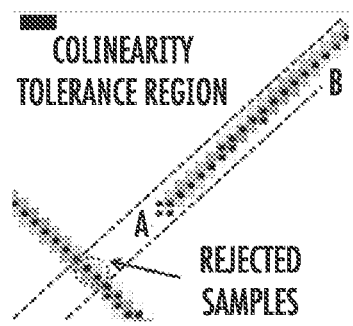
FIG. 2D illustrates a view of RANSAC-based wire-image samples.

FIG. 2A illustrates a flowchart of a wire-based calibration method of the present invention. The flowchart of FIG. 2A starts with identifying a center-line image pixels. RANSAC pixel grouping is done. View-to-view tracking, 3D-2D single view matching, final iterative estimates, and an initial algebraic estimate are also done. FIG. 2B illustrates a graphical view of parameterization of 9-DOF projection view geometry. FIG. 2C illustrates a view of a sampling of wire segment projections, and FIG. 2D illustrates a view of RANSAC-based wire-image samples. The proposed geometric calibration method begins with a scan of the wire phantom to obtain log-scaled projection views in a particular scan geometry. The projection data are then processed in a chain of three main stages.

In the wire projection sampling stage, a search is made in each projection view for integer pixel coordinates approximately traversing the projected center-lines of the wires. Because projection rays passing through a wire's center-line have longer attenuation path lengths than off-centered rays, these pixels can be identified from local maxima in row-wise and column-wise sweeps through the log-scaled image, as illustrated in FIG. 2C. An intensity threshold derived from Otsu's method is used to identify the pixel regions occupied by the wire projections and to restrict the search to those regions.

Once a pool of center-line pixels have been collected, an approach based on the Random Sample Consensus Algorithm (RANSAC) is then used to group the pixels, associating them with different wires. In this process, pixel pairs A and B are randomly drawn from the set S of ungrouped pixels. For each pair of pixels drawn, a search is made in S for further pixels (a so-called consensus set) that lie along a common wire projection containing A and B. Initial candidates for the consensus set are obtained from pixels sufficiently colinear with A and B, as tested using a distance tolerance of $2\sqrt{2}$ pixels from the infinite line passing through A and B, as illustrated in FIG. 2D. A subsequent search, restricted to the tolerance region, is made to reject samples not lying on a common wire with A and B. New pixel pairs are drawn until a sufficiently large consensus set is found, as determined from a preset threshold. When this occurs, it is concluded that a wire has been identified. The pixels for that wire are then removed from the search pool S and the process continues until all wires have been assigned samples. Throughout this work, pixel pitch was in the range 0.3-0.4 mm (2×2 binning of the flat-panel detector described below) and a consensus set threshold of 100 pixels was found to work well for these cases.

Once all pixels lying along a common wire projection have been grouped together, each such group is matched to a particular wire in 3D. This is the 2D-3D mapping segment of the process. To this end, the pixel groups are first used to fit a line segment to each wire projection in each view. This results in the parameterization of each wire projection by a 4D vector $Q_{AB}=[u_A, v_A, u_B, v_B]^T$ where $A=(u_A, v_A)$ and $B=(u_B, v_B)$ are the endpoints of a particular line segment. Note that if the phantom is designed so that the wires form mutually non-coplanar lines in 3D, then their line segment projections can intersect at no more than one point, and therefore their representations $Q_{AB}$ will be very well separated in 4D. The separation between two line segments $Q_{AB}$ and $Q_{CD}$ is quantified as $d(Q_{AB}, Q_{CD})=\min(\|Q_{AB}-Q_{CD}\|, \|Q_{AB}-Q_{DC}\|)$ Using this distance measure, wire projections in adjacent views are compared for proximity and tracked from view to view. This leads to a consistent labelling of each wire's projection across views.

Once view-to-view labelling is established, the wire identification problem reduces to matching each wire projection in a single reference view (e.g. the first view acquired) to its 3D model. By positioning the wire phantom so that, in every scan, it faces the detector in approximately the same pose in the reference view, the wire projections will form predictable patterns of slope, elevation, and intersection in that view. A basic pattern recognition routine customized to the phantom (but not to the source trajectory) can therefore be used to complete the 3D-2D matching. As an example, the image of wire A' in FIG. 1C is always identifiable—assuming very modest repeatability in phantom positioning—as the unique wire image in the lower half of the projection view which is downward sloping. Similarly, the intersection points of each wire with the image boundary in FIG. 2D will always have the same clock-wise ordering. These two features are sufficient to uniquely identify all of the wires. An alternative way to accomplish 3D-2D matching, if an approximate nominal geometry estimate is available, is by direct 3D reconstruction of the wires.

The final stage of the calibration pipeline is to estimate, for each view, the geometry parameters $\alpha$, $\theta$, and C from the set of line coordinate samples $\{x_{ij}\}$ collected previously. Here, $\{x_{ij}\}$ is a 3×1 homogeneous vector denoting the jth pixel coordinate sampled from the ith wire projection in the given view. It is assumed that the wire phantom geometry is known (either from precise design/manufacture or from measurement) with negligible error. In this context, this means that equations for the 3D line $L_i(t)=X_i+tD_i$ passing through each wire, i, are accurately known a priori in some coordinate system.

As a first step in the process, the input data $X_i$, $D_i$, $x_{ij}$, are pre-normalized. The normalization procedure is an adaptation of standard data conditioning methods from conventional point marker-based calibration. Parameter estimates are then obtained by minimizing the least squares cost function, $$f(\alpha, \theta, C) = \sum_{ij} \left| x_{ij}^T K_\alpha^{-T} R_\theta (X_i \times D_i - C \times D_i) \right|^2. \quad (6)$$

The nonlinear least squares residuals are zero, when the samples $x_{ij}$ lie precisely on the modelled lines $l_i=K_\alpha^{-T}R_\theta(X\times D_i-C\times D_i)$. The minimization of f may be accomplished using the Levenberg—Marquardt algorithm, implemented in this work using MATLAB's lsqnonlin command. Note that, unlike BB-based calibration, the above estimation procedure does not use 3D-2D point correspondences. The cost function (6) evaluates a geometry estimate based exclusively on algebraic error, i.e. on how well the wire image pixels $x_{ij}$ satisfy 2D line equations arising from that estimate.

Because it is unclear whether f has local minima, the initializing parameter estimates for the iterative minimization cannot be selected arbitrarily. A two-step analytic algorithm is used for deriving reasonably accurate initial estimates from line fits $l_i$ to the samples $x_{ij}$. The steps are as follows: 1. Using a system of linear homogeneous equations in the elements of P is obtained, with two equations $\hat{l}_i^T P[X_i, D_i]=0$ contributed by each wire. The total system of equations is solved algebraically to give an initial estimate $\hat{P}$ of the projection matrix. The estimate has a decomposition $\hat{P}=K\hat{R}_\theta[1-C]$, except that, because the algebraic solution is unconstrained, K will be a general upper-triangular matrix, rather than one with the specific form. The decomposition of $\hat{P}$ is made using the QR-algorithm, resulting in an estimate $\hat{R}_\theta$ of the detector orientation. 2. Using (4) and (5), and the estimate $\hat{R}_\theta$ obtained in the previous step, the equations are constructed, $$\hat{l}_i^T K_\alpha \hat{R}_\theta X_i = \hat{l}_i^T q \qquad (7)$$

$$\hat{l}_i^T K_\alpha \hat{R}_\theta D_i = 0 \qquad (8)$$

where the change of variables was made $q = K_\alpha \hat{R}_\theta C$. Here again, each wire contributes 2 equations. These equations form a linear system in $\alpha$ and $q$ which are solved to obtain estimates of $\alpha$ and $C = (K_\alpha \hat{R}_\theta)^{-1} q$.

Because this initialization technique involves almost purely algebraic operations, it has the advantages of both speed and flexibility. No specific assumptions about the wire configuration or scan geometry are used, other than that the various equations involved possess well-defined solutions. This will depend on the chosen 3D configuration of wires, as discussed in the next section.

With the geometry estimation procedure above, a solution is obtained with respect to the pre-normalized $X_i$, $D_i$, $x_{ij}$ data. As a final step, the corresponding estimated projection matrix $\hat{P}$ can be mapped back to the original coordinate system as described in the appendix. Estimates of the geometry parameters in the original coordinate system may likewise be obtained from the decomposition of the projection matrix.

As mentioned earlier, an advantageous design choice for a multi-wire calibration phantom is to have the wire segments be mutually non-coplanar, as this avoids fiducial projection overlap in all gantry poses. However, the wire configuration must also be selected so that the geometry estimation is a well-posed inverse problem. While necessary and sufficient conditions are known for an array of point markers to uniquely determine the geometry, a comparable characterization for line-shaped markers has not been previously reported, to the best of our knowledge. Sufficient conditions for invertibility can be deduced, however, from the known theory of vanishing points. This motivated a nominal 8-wire phantom design, as discussed below. The nominal design is depicted in FIG. 1C. Parametric line equation data for the 8 wires are listed in Table 1. A compromise made in this design is the inclusion of parallel, and therefore coplanar, wire pairs. Nevertheless, by spacing the parallel wires sufficiently far apart, fiducial overlap is avoided while still allowing the phantom to accommodate a broad range of circular and non-circular scan trajectories.

The computer vision literature has established (that if a triad of non-degenerate vanishing points $v_i = K_\alpha R_\theta D_i$, $i=1, 2, 3$ from orthogonal directions $D_i$ can be identified in a projection image, then these points can be used to calculate the view geometry. Based on this result, the phantom was designed to contain an orthogonal, mutually non-coplanar set of wires labelled A, B, and C in FIG. 1C with parallel, non co-linear counter-parts A', B', and C'. A gap of 3 cm separates the wire pairs longitudinally so that parallel wires cannot have overlapping projections except for large out-of-plane gantry angulations (about 40° for typical C-arm geometries). The presence of these parallel pairs ensures that 3 vanishing points can be determined from the intersection of their images. This being said, in the interest of incorporating both orthogonally and non-orthogonally oriented wires into the computation, the geometry estimation method does not use established vanishing point methods. However, the option of resorting to vanishing point methods guarantees invertibility, except at gantry poses for which the detector is parallel to one or more of these wires. In such cases, the corresponding vanishing points will be degenerate and the invertibility of the estimation problem is uncertain.

Because the availability of three non-degenerate vanishing points is merely a sufficient condition, it is not clear whether their absence is genuinely a problem. If it is a problem, it is possible that data from additional wires, non-orthogonally oriented with respect to the triad A-A', B-B', C-C', might compensate for information lost when a degenerate view of the triad is reached. With this in mind, an additional pair of parallel wires D-D' oriented at 45° to B-B' and C-C' is included. This choice was based simply on intuition and experimentation; however, in tests of the phantom small calibration errors were observed, even at views where degeneracy occurred.

The proposed calibration method assumes that for each fixed wire, i, line parameters $X_i$, $D_i$ describing the 3D pose of the wire be known a priori with negligible error. This is analogous to traditional BB-based calibration which supposes a known 3D model for the BB locations. With sophisticated manufacturing resources, it may be possible to precisely fabricate the wire phantom so that desired $X_i$, $D_i$ are achieved with high accuracy. An alternative approach is to construct the phantom with approximately desired dimensions and then obtain more precise estimates of $X_i$, $D_i$ from standard circular CBCT scans of the phantom on a well calibrated system. In this work, for the sake of cost and prototyping flexibility, the latter course was followed. The prototype wire phantom, composed of foam blocks and 3D-printed wire mounts, is shown in FIG. 1D. The wires were manually placed to mimic the nominal pose data in Table 1.

An intuitive way to determine the wire poses from a calibrated CT scan is to segment the wires from a 3D CT reconstruction and fit 3D lines to the wire voxels directly. An alternative that works instead with line fits $\hat{l}_i$ to samples $x_{ij}$ extracted from the acquired projection images is used. This leads, as before, to equations (7) and (8), except that in this case, because the CT scan geometry is pre-calibrated, the unknowns in the equations are the wire pose parameters $X_i$ and $D_i$. For each fixed i, two independent linear equations are contributed by each projection view. Solving these linear equations leads to estimates of the wire poses.

Because the 3D parametrization of a line is non-unique, there is a 1D space of solutions $X_i$. Since the geometry estimation cost function of Eq. (6) depends on $X_i$ entirely through $X_i \times D_i$, any point $X_i$ on the line may in theory be selected without affecting the calibration process. For numerical conditioning reasons, however, the chosen $X_i$ should not vary greatly in magnitude from wire to wire. $X_i$ is chosen from the solution space lying approximately at the inner-most wire tips (i.e. the tips closest to the center of the phantom). This was largely a matter of preference, however, and was not intended to accurately represent the wire tip locations.

Applying the above procedure to the phantom in FIG. 1D led to the pose estimates listed in the lower half of Table 1. There are noticeable discrepancies between the nominal and implemented wire poses due to errors in manual placement. Also, because the implemented triad A-A', B-B', C-C' is not ideally orthogonal, it is natural to ask whether the arguments for the design are still valid.

TABLE 1

Wire pose data for nominal phantom design and the estimated poses for the prototype phantom implementation.

|  |  | A | B | C | D | A' | B' | C' | D' |
|---|---|---|---|---|---|---|---|---|---|
| Nominal design | $X_x$ (mm) | 56.10 | 2.08 | 78.08 | −6.73 | 8.66 | 78.08 | 2.08 | −6.73 |
|  | $X_y$ (mm) | −3.79 | 46.08 | 22.08 | −23.63 | 24.16 | −1.71 | −25.71 | 44.00 |
|  | $X_z$ (mm) | 7.73 | 3.34 | 31.13 | 20.31 | −31.06 | −54.46 | −26.66 | −43.63 |
|  | $D_x$ (mm) | 0.0442 | 0.7221 | −0.6904 | 0.0224 | −0.0442 | −0.7221 | 0.6904 | −0.0224 |
|  | $D_y$ (mm) | −0.6906 | 0.5215 | 0.5011 | 0.7231 | 0.6906 | −0.5215 | −0.5011 | −0.7231 |
|  | $D_z$ (mm) | 0.7219 | 0.4546 | 0.5217 | 0.6904 | −0.7219 | −0.4546 | −0.5217 | −0.6904 |
| Implemented prototype | $X_x$ (mm) | 51.40 | 2.44 | 68.01 | −13.34 | 19.28 | 72.20 | 6.22 | 5.40 |
|  | $X_y$ (mm) | −12.99 | 42.78 | 10.75 | −36.05 | 34.60 | 5.73 | −20.80 | 56.65 |
|  | $X_z$ (mm) | 6.45 | 11.25 | 27.15 | 24.75 | −32.25 | −55.05 | −25.65 | −49.95 |
|  | $D_x$ (mm) | 0.0728 | 0.6846 | −0.6346 | 0.0019 | 0.0080 | −0.5706 | 0.6556 | 0.0248 |
|  | $D_y$ (mm) | −0.6691 | 0.5350 | 0.5538 | 0.7012 | 0.6074 | −0.6796 | −0.5902 | −0.8258 |
|  | $D_z$ (mm) | 0.7396 | 0.4951 | 0.5391 | 0.7130 | −0.7944 | −0.4610 | −0.4709 | −0.5634 |

Figure 3A:
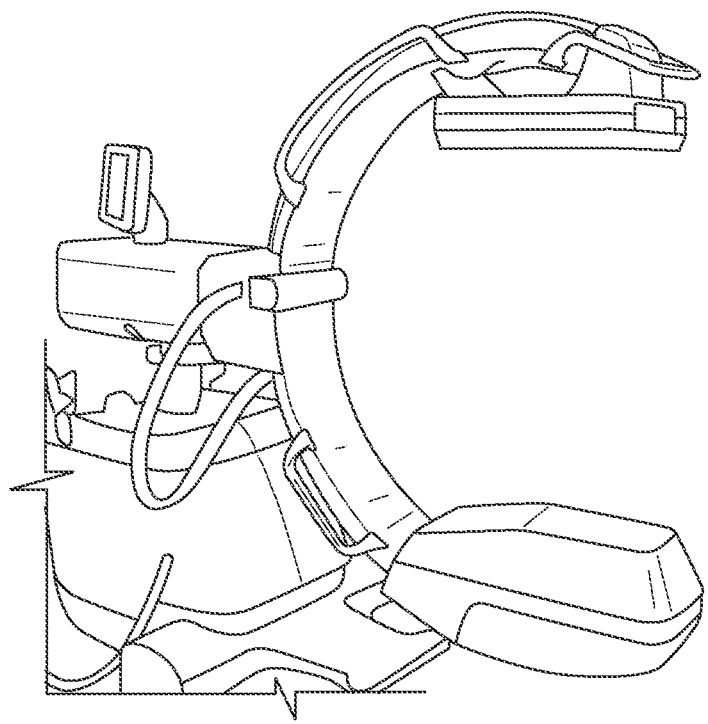
FIG. 3A illustrates a prototype C-arm for CBCT based on the Cios Alpha (Siemens Healthineers)

In exemplary implementations, that are not meant to be considered limiting, the method was tested (Experiment #1) with circular scans made using the prototype C-arm CT system shown in FIG. 3A.

The system was calibrated both with an 8-wire phantom, and with a BB phantom. Both phantoms were of the form and dimensions shown in FIGS. 1A and 1B. FIGS. 1A and 1B illustrate CBCT system geometry calibration phantoms, each with sample 2D projection views. FIG. 1A illustrates a BB phantom with a pair of overlapping marker shadows marked by arrow. FIG. 1B illustrates a proposed wire fiducial phantom, according to an embodiment of the present invention.

The 3D wire poses in the multi-wire phantom were determined using a BB-calibrated scan with this system. Three data sets were acquired. The first was a scan of a set of 4 lead BBs mounted in Styrofoam, well-separated in the field of view both axially and off-axis. Centroid locations were calculated for each marker in each acquired view. Next, a slanted wire phantom (not the 8-wire calibration phantom) was scanned for the purpose of calculating PSF. Finally, a head phantom scan with natural temporal bone detail was acquired (93 kV, 120 mA, 333°/499 views).

The geometry under both calibrations was then used to do the following post-analysis. The 4-BB phantom centroid data was used to calculate Back Projection Error (BPE) for all markers and views. The BPE measures the failure of rays back-projected from a marker's projection shadows to intersect. A best fit 3D intersection of the rays is first computed for each marker. Then, the distance of each ray from this intersection point gives the BPE for that marker and view. FDK reconstructions were made of the slanted wire and head phantoms with 90% hamming filter cut-off and voxel size 0.3 mm. The PSF phantom was used to obtain Gaussian PSF fits at 12 locations in the phantom and the FWHMs were computed.

Figure 3B:
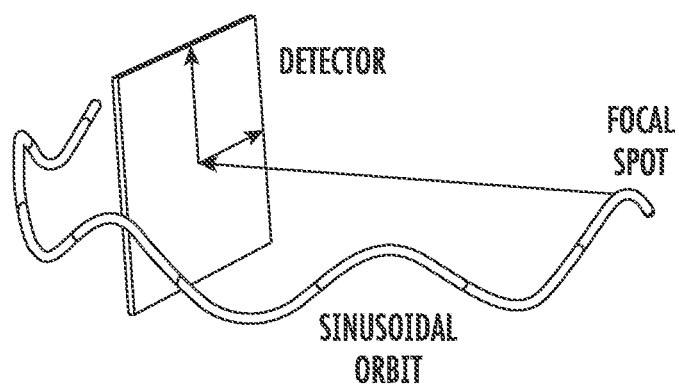
FIG. 3B illustrates a sinusoid-on-sphere orbit used for Experiment #2.

For Experiment #2, simulated scans of a head phantom and an 8-wire calibration phantom were generated in the sinusoid-on-sphere trajectory depicted in FIG. 3B. FIG. 3A illustrates a prototype C-arm for CBCT based on the Cios Alpha (Siemens HealthCare), and FIG. 3B illustrates a sinusoid-on-sphere orbit used for Experiment #2. The pixel pitch for the head scan simulation was 0.616 mm and half that for the wire phantom. The trajectory was derived from a 200°/498 view circular arc based on the Artis Zeego (Siemens Healthcare) robotic C-arm. A sinusoidal series of out-of-plane gantry tilts was then added, such that the peak-to-peak longitudinal variation in source position was 14 cm. Such an orbit was of interest for two reasons. First, improved image quality due to greater axial coverage is expected. Second, it would be challenging to calibrate this orbit with BB phantoms, since large out-of-plane excursions of the gantry increase occurrences of shadow overlap. The head phantom contained 2 stacks of high contrast phantom disk inserts imitating Teflon and polyethylene (see FIG. 5A). The multi-wire calibration procedure was used to compute the geometry, and the head was then reconstructed with 200 iterations of the Penalized Likelihood (PL) algorithm with voxel size 0.5 mm. Huber penalties were used with regularization parameters chosen to match (within 0.5 mm) the resolution of an FDK-reconstructed circular scan at the disk edge nearest the central axial plane.

Resolution at the disk edges was quantified by fitting Gaussian error functions to the disk edge spread function. The derivative of this function gives a local Gaussian PSF whose FWHM was computed for each disk edge as a function of elevation above the equatorial plane. BPE calculations were also made, similar to Experiment #1, but with simulated ground truth projections of 16 markers.

Figure 4A:
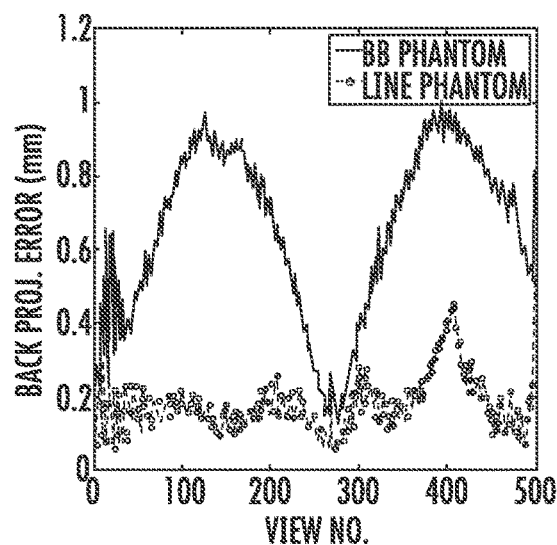
FIGS. 4A-4C illustrate experimental results for Experiment #1, executed with a circular orbit.
Figure 4B:
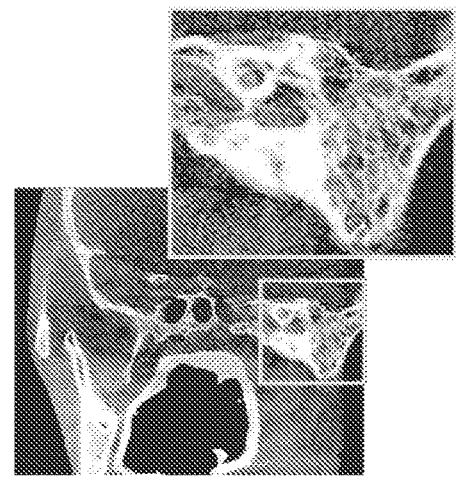
Figure 4C:
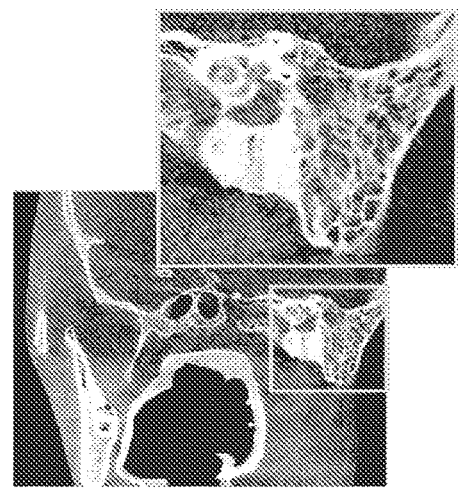

FIGS. 4A-4C illustrate experimental results for Experiment #1, executed with a circular orbit. FIG. 4A illustrates a graphical view of a maximum marker BPE per view for each calibration method. FIG. 4B illustrates an FDK head reconstruction based on BB phantom calibration. FIG. 4C illustrates an FDK head reconstruction based on multi-wire phantom calibration.

The line-based calibration method out-performed calibration via the BB phantom in terms of BPE. Almost uniformly across all views, the worst of the 4 marker BPEs was better for the line phantom and sub-voxel in magnitude. Most of the BPE from the BB method was found to be longitudinal in direction. Since the slanted wires were longitudinally aligned, this higher error was not reflected in the in-plane PSF measurements. All 12 PSF samples where 0.65±0.05 mm for both calibrations. However, the head reconstructions using the BB calibration show more prominent blur and streak, which may be associated with small errors in longitudinal calibration. In any case, the trabecular detail obtained with the line phantom was at least as good as that obtained with the BB phantom.

Figure 5A:
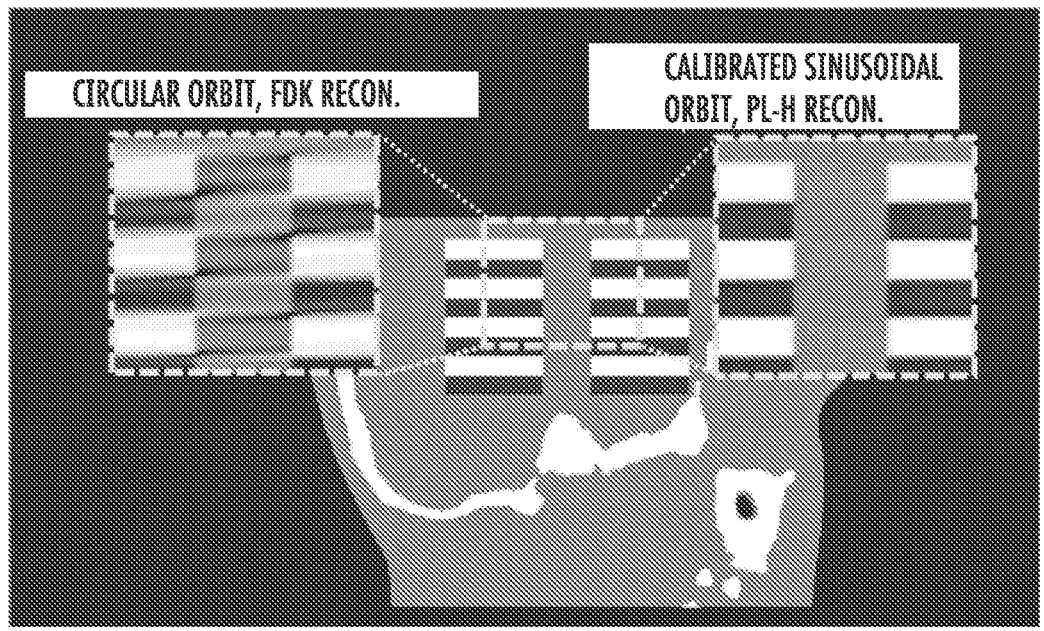
FIGS. 5A and 5B illustrate experimental results for Experiment #2, executed with a noncircular orbit.
Figure 5B:
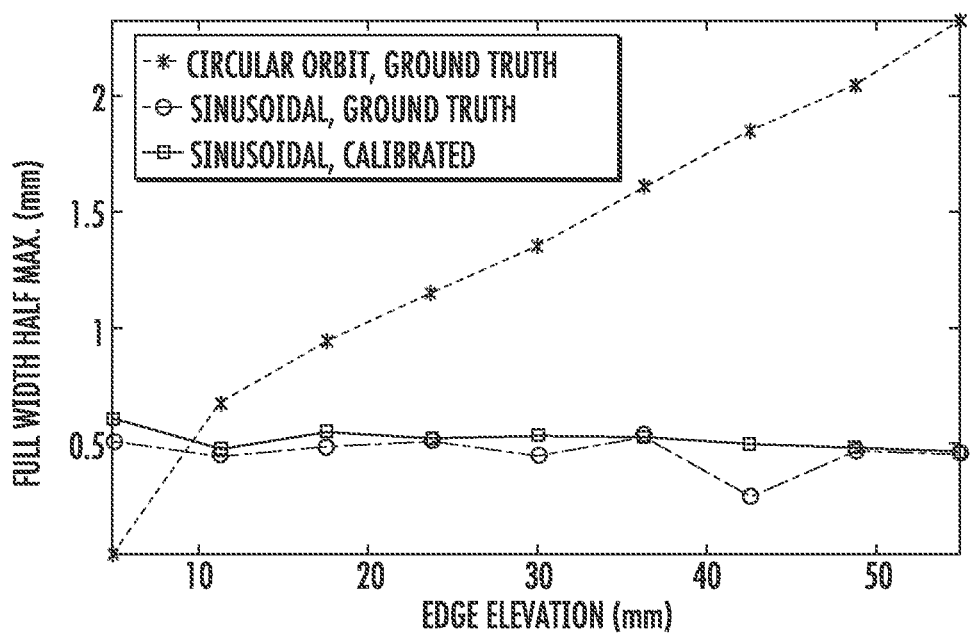

FIGS. 5A and 5B illustrate experimental results for Experiment #2, executed with a noncircular orbit. FIG. 5A illustrates a reconstructions of the head phantom in both a circular and sinusoidal orbit. FIG. 5B illustrates a graphical view of an edge resolution at disk edges as a function of distance from the central axial plane for different orbits. The calibrated reconstruction performed almost indistinguishably from ground truth, both visually and quantitatively. Similar to Experiment #1, BPE results (not shown) were sub-voxel (<0.25 mm) across all views. FIGS. 5A and 5B also compare imaging performance to the FDK-reconstructed circular orbit simulation. This reconstruction used the ground truth geometry, so its inferior performance is entirely attributed to the orbit itself. This highlights the benefit of a noncircular orbit for certain imaging tasks.

Figure 6A:
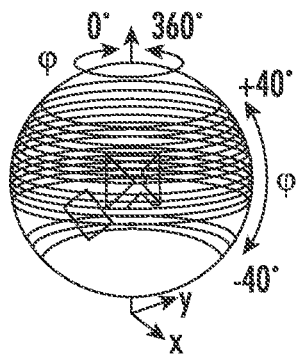
FIGS. 6A-6E illustrate views of experimental methods for Experiments 3A, 3B, 4, and 5.
Figure 6B:
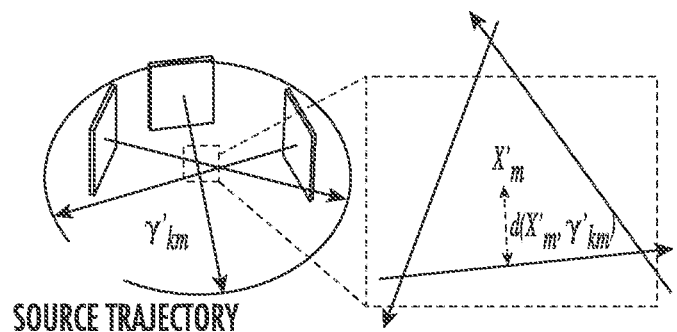
Figure 6C:
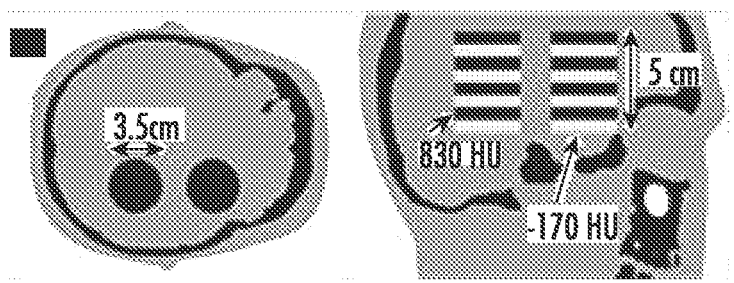
Figures 6D, 6E:
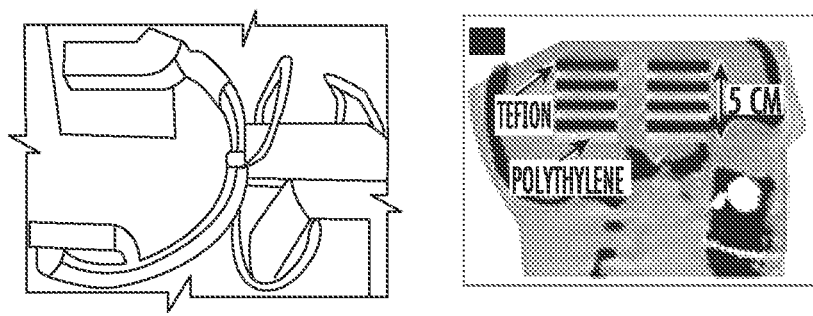

FIGS. 6A-6E illustrate views of experimental methods for Experiments 3A, 3B, 4, and 5. FIG. 6A illustrates a sampling of gantry poses in spherical coordinates used in calibration accuracy simulation tests. FIG. 6B illustrates a triangulation ray deviation metric. FIG. 6C illustrates a digital head phantom with two stacks of high contrast disks. FIG. 6D illustrates a prototype mobile C-arm for cone beam CT based on the Cios Alpha. FIG. 6E illustrates a real head phantom with two stacks of polyethylene and Teflon® disks. As with the previous experiments, the experiments that follow are not meant to be considered limiting and are included only to further illustrate the invention.

In a first set of simulation tests for Experiment #3A, the extent to which the 8-wire configuration provided accurate estimates of various gantry poses was examined. Synthetic line projection samples $x_{ij}$ of our prototype wire phantom implementation (with pose data $X_i$, $D_i$ from the lower part of Table 1, not the nominal design) were generated for a hypothetical isocentric C-arm geometry with a 40 cm×40 cm detector area and 0.308 mm pixel pitch. In the ground truth geometry, the SDD was 120 cm and the source-isocenter distance (SID) was 78.5 cm. Data were generated, as illustrated in FIG. 6A, for a range of gantry angulations uniformly sampled in spherical coordinates. The sampling was at 2° increments with respect to both in-plane azimuthal gantry positions, $0° \leq \varphi \leq 360°$, and out-of-plane gantry elevations, $-40° \leq \psi \leq 40°$. The range of gantry elevations considered here is consistent with anti-collision constraints in typical scan scenarios. Out-of-plane elevations greater than 40° would normally risk gantry collision with the patient or table.

The samples $x_{ij}$ were generated from noise-free, analytic projections of the wires under the known ground truth geometry. To these, 50 realizations of Gaussian errors were then added so as to displace them perpendicularly from the true ith wire location. The number of samples along the length of each wire projection was selected as max (H, W), where H and W are the height and width of the wire projection in pixels. The variance of the Gaussian noise was chosen to produce root mean squared (RMS) perpendicular deviations from the true line of 0.093 mm (or 0.30 pixels). This choice was in agreement with RMS line fit residuals observed in actual wire phantom scans (at 70 kV, 100 mAs) taken on the mobile C-arm, as illustrated in FIG. 5D. Geometry estimates were then derived from each of the 50 realizations. The tests here focused exclusively on the geometry estimation step and not the full processing chain. It is for this reason that the samples were generated directly and not from simulated x-ray images.

The accuracies of the geometry estimates were first assessed in terms of magnification-corrected reprojection error (RPE), a forward projection accuracy metric:

$$\text{Mag. Corrected } RPE = \frac{d(\hat{P}X, PX)}{SDD/\text{depth}(X)}.$$

Here, $d(\hat{P}X, PX)$ is the Euclidean distance between the ideal forward projection PX of a 3D test point X and its estimated projection $\hat{P}X$. This is normalized by SDD/depth(X), the usual cone beam magnification at X. This was evaluated, for all 50 realizations and gantry positions, for a set of 16 test points distributed over a 13×13×11 cm³ region of the FOV.

In further simulations of the same gantry geometry, synthetic $x_{ij}$ were generated for the three scan orbits (circular short scan, sinusoid-on-sphere, and task-driven). The circular and sinusoidal orbits consisted of a 200°/498 view arc in-plane. The sinusoid-on-sphere trajectory was then derived by adding a sinusoidally-varying series of out-of-plane gantry tilts to the circular trajectory with a 5° amplitude. This amplitude was sufficient to produce a 14 cm peak-to-peak longitudinal variation in the x-ray source position. The task-driven orbit consisted of 336 views.

Repeated calibrations of these orbits were then performed, again for 50 realizations of $x_{ij}$ with 0.30 pixel simulated errors. The orbit calibrations were then assessed quantitatively in terms of two forms of backprojection error metric—the ray deviation, d, and triangulation error, Δ. The same set of 16 test points were forward projected using ground truth geometric knowledge of the orbits. The 50 geometry estimates were then used to triangulate the locations of the 16 points from their projected coordinates, as illustrated in FIG. 6B. The triangulated position of the $m^{th}$ test point $X_m^*$ was obtained as the linear least squares solution to, $$X_m^* = \arg\min x \sum_k d^2(X, r_{km})$$

where $d(\cdot, r_{km})$ is the Euclidean distance to $r_{km}$, the back-projected ray from the mth test point projection in the kth view. The triangulation error was then computed as $$\Delta = \|X_m^* - X_m\|$$

where $X_m$ is the ground truth location of the $m^{th}$ marker. The ray deviations were computed as $d(X_m^*, r_{km})$. In other words, they measure the spread of the rays around the triangulated point, and hence the degree of distortion likely to propagate into CT image reconstruction from backprojection error. Lastly, for the same 3 orbits above and the various noise realizations mentioned, errors were computed in the source position, the pose of the detector panel, and the magnification SDD/depth(X) at the 16 test points.

Figure 7C:
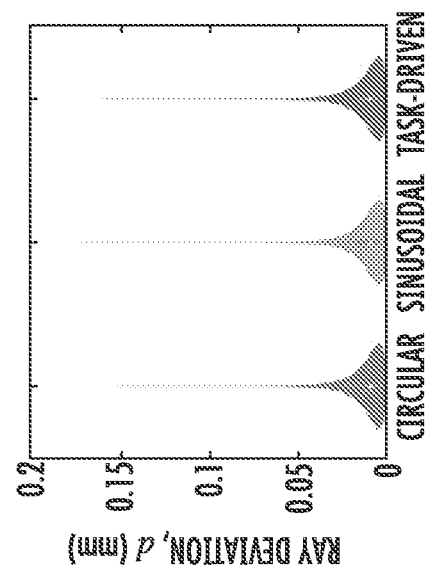
FIGS. 7A-7C illustrate graphical views of geometry estimation accuracy: distributions of various forward and back projection errors.
Figure 7B:
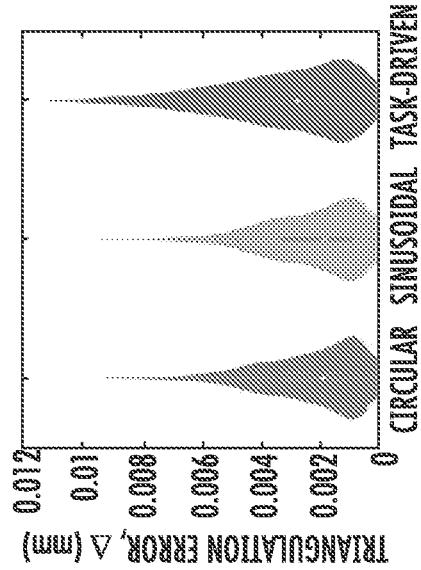
Figure 7A:
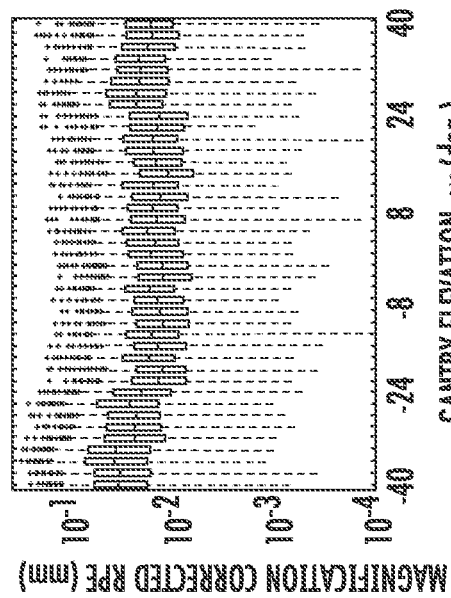

Results of Experiment #3A are summarized in FIGS. 7A-7C. FIGS. 7A-7C illustrate graphical views of geometry estimation accuracy: distributions of various forward and back projection errors. All are based on 50 independent noise realization. FIG. 7A illustrates a box plot of magnification-corrected RPE at various out-of-plane gantry elevations, ψ computed from samples over both noise realizations and test points. At each elevation, worst-case distributions are shown, meaning the distribution for the azimuthal position with the largest outliers. FIG. 7B illustrates violin plots of triangulation error, Δ, computed from samples over all noise realizations, test points, and views. Median and interquartile range are also shown in each case. FIG. 7C illustrates the same for ray deviation, d. The worst-case RPE distributions had median values consistently less than 0.1 mm at all gantry elevations, and an overall maximum error (0.37 mm) that is considerably less than the voxel size (~0.5 mm) typical for C-arm cone-beam CT. The wire-based calibrations showed similarly high back projection accuracy for the three orbit geometries considered. Triangulation error was consistently less than 0.012 mm for all noise realizations and markers. Similarly, the ray deviation exhibited a median value of ~0.01 mm for all orbits and was consistently below 0.2 mm for all realizations, markers, and projection views.

Finally, the errors in magnification and source-detector pose are reported for the three orbits in Table 2. For present purposes, the source coordinates $C=[c_u, c_v, c_w]^T$ and the location of the detector center $FP=[FP_u, FP_v, FP_w]^T$ are expressed with respect to rotated axes that align with the ground truth detector axes $[R_{\theta,u}, R_{\theta,v}, R_{\theta,w}]^T$. In this coordinate system, one can more easily see how depth-related pose parameters ($c_w$ and $FP_w$) are an order of magnitude more error-sensitive than other parameters. Errors in detector orientation have been quantified in terms of two metrics: angular discrepancy between the ground truth and estimated detector axis $R_{\theta,w}$, which indicates the orientation of the central ray; and the error in panel skew, i.e. the orientation angle within the detector plane of the pixel rows/columns. The latter is known to have more significant impact on image reconstruction than other detector orientation parameters. Error performance reported in Table 2 is similar to, and in some cases exceeds, previously reported results for BB-based methods. In particular, source location, detector location, and skew all show less error for circular orbits.

$$ESF(z) = a + \frac{b}{2}\left(1 + \text{erf}\left(\frac{z - z_0}{\sigma\sqrt{2}}\right)\right)$$

to the edge spread function (ESF) of the flat disk boundaries, with the a parameter serving as a measure of ESF width. The same procedure was applied to the simulated circular orbit, except that the ground truth geometry was used in the PWLS reconstruction. Both reconstructions used a voxel size of 0.6 mm. Regularizing penalty weights were chosen to approximately match ESF width to $\sigma=0.1$ mm at the disk edge nearest the central axial plane for the circular and sinusoidal reconstructions. PWLS cost function minimizations were implemented with 20 iterations of the OS-MOM2 algorithm with 10 ordered subsets. To facilitate comparison, both iterative reconstructions were initialized with the same volume, reconstructed from the circular orbit using the Feldkamp-Davis-Kress (FDK) algorithm. In realistic sinusoidal scans, an initial reconstruction would be obtained from an analytic reconstruction algorithm appropriate to the sinusoidal orbit shape.

Figure 8A:
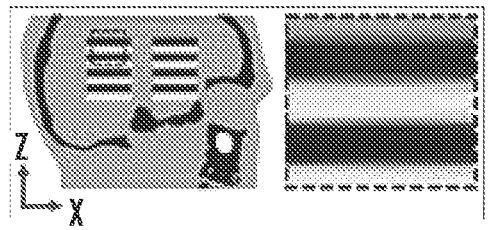
FIGS. 8A-8C illustrate graphical views of simulated integration into a CBCT imaging chain.
Figure 8B:
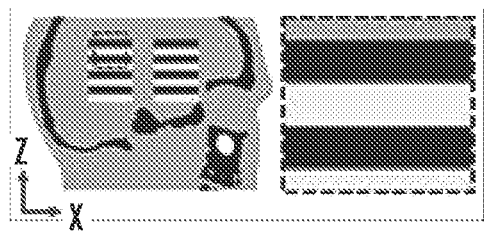
Figure 8C:
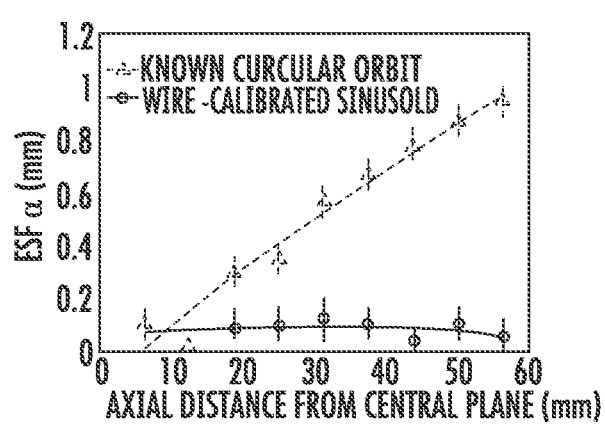

The image reconstructions for the digital head phantom are shown in FIGS. 8A-8C. In FIG. 8A cone-beam artifacts

TABLE 2

Errors in magnification and various source-detector pose parameters from simulated wire-based calibration for serveral orbit geometries.
Error mean and standard deviation are take with respect to 50 measurments over all orbit views. Magnification was compared from 16 test points.

| | | Source location (mm) | | | Detector center (mm) | | | Detector orientation (deg) | | |
|---|---|---|---|---|---|---|---|---|---|---|
| | | $c_u$ | $c_v$ | $c_w$ | $FP_u$ | $FP_v$ | $FP_w$ | $R_{\theta,w}$ | Skew | Mag. (%) |
| Circular | Mean | 0.066 | 0.088 | 1.145 | 0.032 | 0.044 | 0.581 | 0.092 | 0.002 | 0.014 |
| | Std Dev | 0.073 | 0.081 | 0.933 | 0.033 | 0.040 | 0.456 | 0.053 | 0.002 | 0.013 |
| Sinusoidal | Mean | 0.063 | 0.087 | 1.157 | 0.030 | 0.044 | 0.588 | 0.092 | 0.004 | 0.014 |
| | Std Dev | 0.066 | 0.077 | 0.943 | 0.030 | 0.038 | 0.462 | 0.053 | 0.004 | 0.013 |
| Task-driven | Mean | 0.100 | 0.068 | 1.274 | 0.050 | 0.034 | 0.642 | 0.096 | 0.030 | 0.015 |
| | Std Dev | 0.113 | 0.065 | 1.017 | 0.057 | 0.032 | 0.513 | 0.067 | 0.028 | 0.014 |

On the whole, these results support the basic feasibility of the wire calibration method, showing it to be robust to realistic levels of noise in the projection data over a wide range of gantry poses. Note also that the calibration remained accurate even at views that should have had degenerate vanishing points in an ideal implementation of the wire phantom. In the circular orbit, for example, the detector plane undergoes a rotation greater than 180° and therefore becomes parallel to each wire segment at some point during the rotation.

In a second simulation study Experiment #3B, the full calibration pipeline was applied to the imaging of a digital head phantom. The phantom contained two stacks of high contrast disks of alternating intensity (830 HU and −170 HU). Synthetic projection views with pixel pitch 0.616 mm were generated for the digital head in both the circular and sinusoidal orbits of using a trilinear interpolating forward projector. Projections of the 8-wire calibration phantom with pixel pitch 0.308 mm phantom were simulated in the sinusoidal orbit using analytic line integrals. No projection noise was added, since the phenomena of interest in this particular experiment were exclusively geometric.

The multi-wire calibration procedure was used to compute the sinusoidal geometry, and the head was then reconstructed from the sinusoidal orbit projections with the penalized weighted least squares (PWLS) model-based algorithm. Axial resolution was quantified by fitting Gaussian error functions associated with the incomplete geometry of the circular scan are evident as blur (in the z direction) for each disk, particularly at increased distance from the central axial plane. Conversely, in FIG. 8B, the sinusoid-on-sphere orbit yields an image reconstruction with sharp edge resolution and an absence of cone-beam artifacts, as expected for this scan geometry if accurately calibrated. These observations are also reflected quantitatively in FIG. 8C, where the ESF width ($\sigma$) is plotted versus distance from the central axial plane. The results illustrate successful application of the wire-based calibration method for a non-circular orbit known to have beneficial image quality characteristics. FIGS. 8A-8C illustrate graphical views of simulated integration into a CBCT imaging chain. These figures illustrate images of the digital head phantom reconstructed using the PWLS algorithm for FIG. 8A as a known circular scan geometry and FIG. 8B as a sinusoid-on-sphere geometry calibrated with the wire-based calibration method. FIG. 8C illustrates a plot of ESF width $\sigma$ as a function of distance from the central axial plane.

The proposed wire-based calibration method was compared to conventional BB-based calibration in real circular scans performed using the prototype C-arm in Experiment #4. The system has an SDD of approximately 110 cm, an SID of 65 cm, and a 30 cm×30 cm detector area. Geometric calibrations of this system were performed with both the 8-wire phantom and the 2-ring BB phantom. Like the simulated version, the BB-phantom was of diameter 10 cm with 8 BBs in each ring and a ring separation of 9 cm. For the BB-based calibrations, parameter estimates were obtained using a standard iterative least squares approach using the Levenberg-Marquardt algorithm.

Three data sets were acquired. The first was a scan of a triangulation target phantom, consisting of 4 spherical lead markers mounted on a flat foam surface. The triangulation markers were spread over a 12 cm lateral by 12 cm longitudinal area of the 16 cm×16 cm×14 cm field of view (FOV). Centroid locations were calculated for each marker in each acquired view and used to triangulate the 4 markers. Triangulation ray deviations were thus computed for both calibration methods. The difference between the triangulated marker locations, as determined from the wire-based and BB-based calibrations, was also calculated.

Next, a phantom containing several slanted wires (0.1 mm diameter steel—not the 8-wire calibration phantom) was scanned for the purpose of calculating point spread function (PSF). FDK reconstructions using both calibrations were made of the phantom with 90% Hamming filter cut-off frequency and voxel size 0.3 mm. Gaussian PSF fits were then derived from samples taken from 45 sub-volumes, each approximately 1 cm$^3$ and centered around different sections of slanted wire. Finally, a head phantom with natural temporal bone detail was imaged (93 kV, 120 mAs, 350°/560 views). FDK reconstructions using both calibrations were performed, again with 90% Hamming filter cut-off frequency and voxel size 0.3 mm.

FIGS. 9A-9D summarizes the results of Experiment #5, demonstrating ray deviation, of FIG. 9A, with a median value of 0.07 mm for the BB-based calibration and 0.05 mm for the wire-based calibration. The latter exhibits a distribution in ray deviation that was significantly lower ($p \ll 0.001$) than for BB calibration, particularly in the tails of the distribution for which the BB calibration exhibited outlier ray deviations up to 0.35 mm. The difference between the two methods—while statistically significant—is too small to have a major impact on the quality of CT image reconstruction. Such is evident in the visualization of fine details in images of the temporal bone in FIGS. 9C and 9D, which are visually indistinguishable. Once again, wire-based calibration showed uniformly low triangulation error, in spite of the possibility of degenerate vanishing points. FIGS. 9A-9D illustrate image and graphical views of a comparison with BB-based calibration in a real circular scan orbit. FIG. 9A illustrates a distribution of ray deviation for BB and wire calibration methods as measured with a 4-marker phantom. The ensembles range over gantry positions and markers. FIG. 9B illustrates a distributions of the FWHM in PSF for the two calibration methods. The images show FDK reconstructions of a head phantom in FIG. 9C of a BB-based calibration and FIG. 9D shows a wire-based calibration.

Wire-based calibration also demonstrated a slight improvement ($p \ll 0.001$) in the PSF width as evident in FIG. 9B. Overall, the results demonstrate the applicability of the wire-based calibration method in real data, showing imaging performance equivalent to that with conventional BB-based calibration.

The wire-based calibration method was tested on a real, non-circular trajectory implemented on the mobile C-arm CT prototype in Experiment #6. The C-arm was equipped with an external motion controller capable of driving the arm in pre-programmed sequences of propeller and orbital rotations. The nominal orbit was a 3-arc sequence consisting of a 200° propeller rotation (equivalent to 180°+fan angle), followed by a 6° orbital/longitudinal rotation, and finally a 160° propeller rotation with the gantry remaining at a 6° orbital tilt. The increased axial coverage of this orbit gives similar benefits relative to a circular scan as seen for the sinusoidal orbit in Experiment #4. A convenience of this choice of scan geometry is that an FDK initializer for iterative reconstruction can be readily derived from the 200° arc.

The head phantom was scanned in this orbit at 90 kV, 170 mAs. A circular scan at 90 kV, 120 mAs was also acquired. Similar to Experiment #4, the phantom contained two stacks of high contrast polyethylene and Teflon disks. The head phantom was centered longitudinally on the plane of the circular scan and on the plane of the initial 200° section of the 3-arc scan. Quadratically penalized poisson likelihood (PPL) reconstructions were made from both scans with cost function minimizations implemented with 20 iterations of the OS-SQS algorithm with 10 ordered subsets. The circular scan was reconstructed using a BB-based calibration to imitate a conventional CT imaging chain, while the 3-arc scan used wire-based calibration. Both iterative reconstructions were initialized with an FDK image derived from an initial 180°+fan arc. ESF fits to the disk edges were also made as in Experiment #1B and were used to verify approximate resolution matching in the two reconstructions at the disk edge nearest to the central axial plane of the head phantom.

Figure 10A:
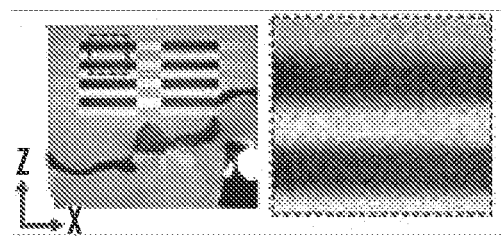
FIGS. 10A-10C illustrate application to a three-arc orbit on a mobile C-arm.
Figure 10B:
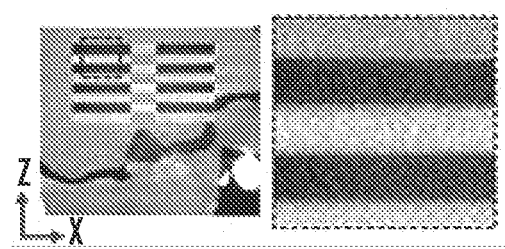
Figure 10C:
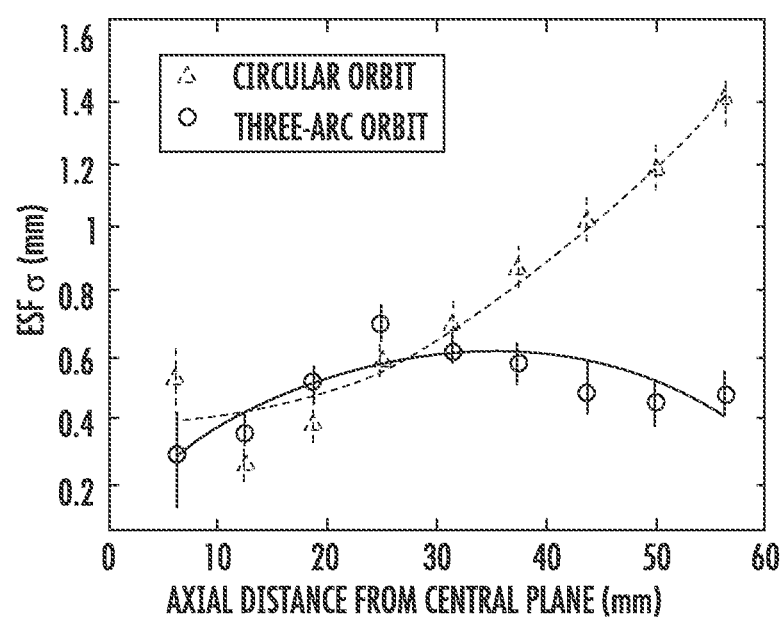

FIGS. 10A-10C illustrate application to a three-arc orbit on a mobile C-arm. FIG. 10A illustrates sagittal images of a head phantom (reconstructed using the PPL algorithm) containing stacks of disks, scanned using a circular trajectory with geometric calibration by the BB method. FIG. 10B illustrates the same, scanned using the three-arc orbit with geometric calibration by the wire method. FIG. 10C illustrates a plot of ESF width $\alpha$ as a function of distance from the central axial plane. shows the results of Experiment #3 involving a head phantom imaged with a mobile C-arm using circular and non-circular orbits. The results largely mirror those of Experiment #4. As expected, the non-circular (three-arc) orbit exhibits superior sampling characteristics compared to a circular orbit, evident in improved resolution of disk edges in the z-direction. Each case exhibits streak artifacts that were not observed in Experiment #4, associated with non-geometric effects such as beam hardening. As shown in FIG. 10C, the non-circular orbit better maintains ESF width ($\sigma$) as a function of distance (z) from the central axial plane. The results demonstrate the wire calibration method in real data and validate its utility in application to non-circular orbits of a form that are becoming increasingly prevalent with advanced C-arm systems to improve image quality and expand FOV.

This work shows successful implementation of a new geometric calibration method applicable to both conventional circular orbits and to non-conventional, non-circular orbits that challenge existing BB-based methods. Future work will include optimizing the line fiducial configuration and application to other non-circular scans.

The present invention may be carried out using a computer, non-transitory computer readable medium, or alternately a computing device or non-transitory computer readable medium incorporated into the scanner. Indeed, any suitable method of calculation known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

The computing device can be a special computer designed specifically for this purpose. The computing device can be unique to the present invention and designed specifically to carry out the method of the present invention. Scanners generally have a console which is a proprietary master control center of the scanner designed specifically to carry out the operations of the scanner and receive the imaging data created by the scanner. Typically, this console is made up of a specialized computer, custom keyboard, and multiple monitors. There can be two different types of control consoles, one used by the scanner operator and the other used by the physician. The operator's console controls such variables as the thickness of the image, the amount of tube current/voltage, mechanical movement of the patient table and other radiographic technique factors. The physician's viewing console allows viewing of the images without interfering with the normal scanner operation. This console is capable of rudimentary image analysis. The operating console computer is a non-generic computer specifically designed by the scanner manufacturer for bilateral (input output) communication with the scanner. It is not a standard business or personal computer that can be purchased at a local store. Additionally this console computer carries out communications with the scanner through the execution of proprietary custom built software that is designed and written by the scanner manufacturer for the computer hardware to specifically operate the scanner hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention. While exemplary embodiments are provided herein, these examples are not meant to be considered limiting. The examples are provided merely as a way to illustrate the present invention. Any suitable implementation of the present invention known to or conceivable by one of skill in the art could also be used.

What is claimed is:

1. A method of calibration for an imaging scanner comprising:
   providing line shaped markers for the imaging scanner, such that the line shaped markers are represented by a line in the image;
   programming a non-transitory computer readable medium to execute steps comprising:
      describing a 3D pose of the line shaped markers;
      extracting sample points along a 2D shadow of each of the line shaped markers to map the 3D pose to a 2D line; and
      estimating geometric parameters for the imaging scanner from the aforementioned 3D line pose and 2D extracted sample points.

2. The method of claim 1 further comprising the imaging scanner having a sinusoidal orbit.

3. The method of claim 1 further comprising estimating the geometric parameters by minimizing one selected from a group consisting of a least squares cost function, a modified cost function, or a weighted least squares function.

4. The method of claim 1 wherein the line shaped markers take the form of radiopaque wires.

5. The method of claim 1 wherein the imaging scanner has a circular or non-circular orbit or is capable of multiple orbits of different shapes.

6. The method of claim 1 wherein the imaging scanner takes the form of one selected from a group consisting of a computed tomography scanner and a cone-beam computed tomography scanner.

7. The method of claim 1 further comprising executing pose determination.

8. The method of claim 7 further comprising executing pose determination from a limited orbit.

9. The method of claim 7 further comprising executing pose determination from a single view.

10. The method of claim 1 further comprising using the method for tomosynthesis.

11. The method of claim 1 further comprising executing a single view.

12. The method of claim 11 further comprising executing the single view for 3D-2D registration.

13. A system for calibration for a computed tomography scanner comprising:
    line shaped markers for the computed tomography scanner, wherein the computed tomography scanner to be calibrated has a circular or non-circular orbit or is capable of multiple orbits of different shapes, such that the line shaped markers are represented by a line in the image;
    a non-transitory computer readable medium programmed to execute steps comprising:
       describing a 3D pose of the line shaped markers;
       extracting sample points along a 2D shadow of each of the line shaped markers to map the 3D pose to a 2D line; and
       estimating geometric parameters for the computed tomography scanner from the aforementioned 3D line pose and 2D extracted sample points.

14. The system of claim 13 further comprising the computed tomography scanner having a sinusoidal orbit.

15. The system of claim 13 further comprising the non-transitory computer readable medium being programmed for estimating the geometric parameters by minimizing a least squares cost function.

16. The system of claim 13 wherein the line shaped markers take the form of radiopaque wires.

17. The system of claim 13 wherein the computed tomography scanner has a circular or non-circular orbit or is capable of multiple orbits of different shapes.

18. The system of claim 13 wherein the computed tomography scanner takes the form of one selected from a group consisting of a computed tomography scanner and a cone-beam computed tomography scanner.

19. The system of claim 13 further comprising the non-transitory computer readable medium being programmed for executing pose determination.

20. The system of claim 13 further comprising executing pose determination from a limited orbit.

* * * * *

UNITED STATES PATENT AND TRADEMARK OFFICE
CERTIFICATE OF CORRECTION

PATENT NO. : 11,478,214 B2  
APPLICATION NO. : 16/494439  
DATED : October 25, 2022  
INVENTOR(S) : Jeffrey H. Siewerdsen, Matthew W. Jacobson and Michael Ketcha Page 1 of 1

It is certified that error appears in the above-identified patent and that said Letters Patent is hereby corrected as shown below:

In the Specification

Column 1, Line 4-13, should read:
CROSS-REFERENCE TO RELATED APPLICATIONS
This application is a 35 U.S.C. § 371 U.S. national entry of International Application PCT/US2018/022809, having an international filing date of March 16, 2018, which claims the benefit of U.S. Provisional Application No. 62/472,178, filed March 16, 2017, the content of each of the aforementioned applications is herein incorporated by reference in their entirety.

Signed and Sealed this
Fourteenth Day of January, 2025

Derrick Brent
*Acting Director of the United States Patent and Trademark Office*